Figure 1:
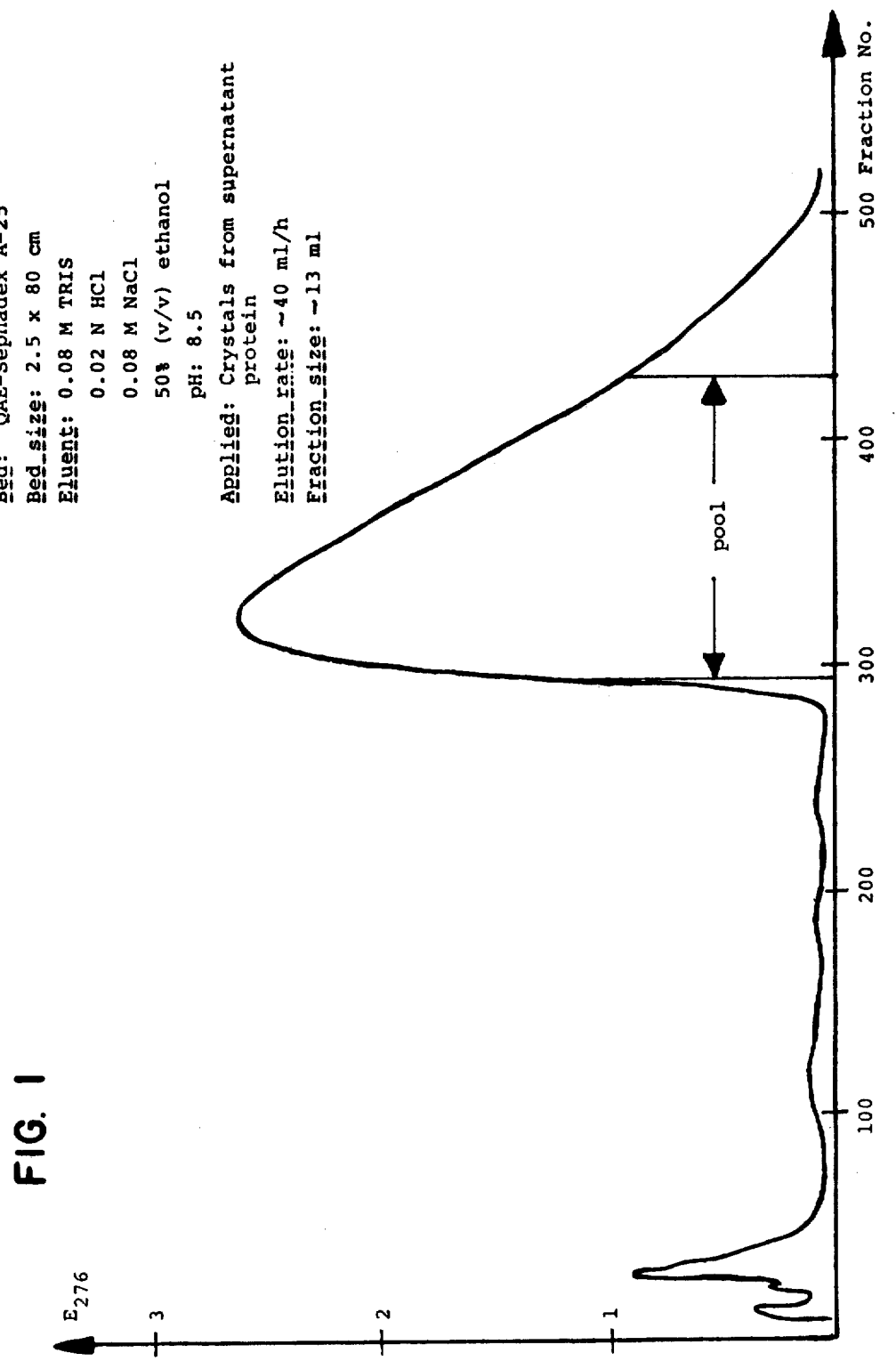

United States Patent [19]

Jorgensen et al.

[11]  4,370,317

[45]  Jan. 25, 1983

[54] PANCREATIC SPASMOLYTIC POLYPEPTIDE

[75] Inventors: Klavs H. Jorgensen, Virum; Karin D. Jorgensen, Vedbaek; Lars Thim, Gentofte, all of Denmark

[73] Assignee: Novo Industri A/S, Denmark

[21] Appl. No.: 241,851

[22] Filed: Mar. 9, 1981

Related U.S. Application Data

[63] Continuation-in-part of Ser. No. 185,796, Sep. 10, 1980, abandoned.

[51] Int. Cl.³ .............................................. A61K 37/00
[52] U.S. Cl. .................................................... 424/177
[58] Field of Search ......................................... 424/177

[56]  References Cited
FOREIGN PATENT DOCUMENTS 924815  5/1963  United Kingdom ................ 424/177

Primary Examiner—Delbert R. Phillips
Attorney, Agent, or Firm—Fidelman, Wolffe & Waldron

[57]  ABSTRACT

The invention relates to a novel purified polypeptide which is recoverable from porcine pancreas glands. The amino acid composition of the said polypeptide has been determined to be as follows:

Trp (2), Lys (4), His (1), Arg (5), Asx (10), Thr (3), Ser (9), Glx (12), Pro (12), Gly (6), Ala (6), Cys 1/2 (14), Val (7), Met (2), Ile (3), Leu (1), Try (2), Phe (7), wherein the determinations are subjected to the usual error of ±10 percent of the indicated figures. The partial amino acid sequence comprising a total of 45 amino acids from the N-terminal, is believed to be:

pyrGlu-Lys-Pro-Ala-Ala-Cys-Arg-Cys-Ser-Arg-Glx-
                     5                              10

-Asx-Pro-Lys-Asx-Arg-Val-Asx-Cys-Gly-Phe-Pro-Gly-Ile-Thr-
              15                   20                     25

-Ser-Asx-Glx-Cys-Phe-Thr-Ser-Gly-Cys-Cys-Phe-Asx-Ser-Glx-Val-
              30                   35                     40

-Pro-Gly-Val-Pro-Trp-,
                          45 wherein pyrGlu (residue 1) stands for pyroglutamic acid.

The purified polypeptide is of utility as a medicament, for example as a spasmolytic agent, as an agent for treatment of gastroduodenal ulcers and as a diagnostic aid.

11 Claims, 2 Drawing Figures

PANCREATIC SPASMOLYTIC POLYPEPTIDE

This application is a continuation-in-part of Ser. No. 185,796, filed Sept. 10, 1980, now abandoned.

This invention is directed to a novel purified polypeptide or a physiologically acceptable salt thereof, as well as to a method for recovery and purification thereof and to the use thereof as a medicament. The purified polypeptide of this invention, which is recoverable from porcine pancreas, has surprisingly been shown to possess smooth muscle relaxing or spasmolytic effects. It has, therefore, been accorded the trivial name of Pancreatic Spasmolytic Polypeptide, hereinafter for the sake of convenience abbreviated to PSP. Besides, PSP has surprisingly been found to possess an inhibitory effect on gastric acid secretion.

RATIONALE OF THE INVENTION

Spasmolytic agents or antispasmodics, such as atropine, congeners thereof and synthetic drugs having an atropine-like effect, are widely used for the treatment of a variety of ailments, in particular of smooth muscle spasms and hypermotility states. However, the intended action of such drugs is usually accompanied by a number of side effects attributable to their general character of being anticholinergics.

As a diagnostic aid in gastrointestinal radiology, particularly in conjunction with an X-ray visualization medium for improving visualization of the gastrointestinal, biliary and urinary tracts, atropine-like anticholinergic drugs have also been commonly used. Such a drug is usually administered parenterally and, owing to the size of the dose needed to induce relaxation, the side effects classical to those agents are usually encountered.

Recently, parenteral administration of the peptide hormone glucagon consisting of 29 amino acids was introduced as an alternative means of reducing gastrointestinal motility in conjunction with radiographic examinations (vide U.S. Pat. No. 3,862,301). However, glucagon exerts a plurality of actions in the human body including a strong influence on metabolic regulatory functions, the most conspicuous effects being the induction of hyperglycemia and lipolysis. Thus, although the introduction of glucagon in endoscopy provided certain advantages, undesirable side effects were not completely abolished.

As an example of a known medicament which is used to inhibit gastric acid secretion, cimetidin may be mentioned. However, cimetidin possesses frequent adverse effects such as diarrhoea, exanthema, elevation of liver enzymes, and gynecomastia. As PSP is a polypeptide which is to be dosed orally and as it is not absorbed in substantial amounts in the gastrointestinal tract, it is not likely to have systemic adverse effects.

It is an object of this invention to provide a spasmolytic agent which, whilst possessing antispasmodic and smooth muscle relaxing effects comparable to those of known agents, exhibits substantially reduced side effects as compared to glucagon and atropine at least.

Apart from the spasmolytic effects of PSP, the peptide possesses an inhibitory effect on gastric acid secretion. Patients with duodenal ulcers benefit from treatment with agents which inhibit gastric acid secretion. However, the same patients suffer from an increased gastrointestinal motility. PSP combines two effects which are highly desirable in the treatment of patients with duodenal ulcers, an inhibitory effect on the gastrointestinal motility, and an inhibitory effect on gastric acid secretion.

STATEMENT OF THE INVENTION

According to one aspect of the present invention there is provided a novel purified polypeptide exhibiting the following amino acid composition:

Trp (2), Lys (4), His (1), Arg (5), Asx (10), Thr (3), Ser (9), Glx (12), Pro (12), Gly (6), Ala (6), Cys ½ (14), Val (7), Met (2), Ile (3), Leu (1), Tyr (2), Phe (7), wherein the determinations are subjected to the usual error of ±10 percent of the indicated figures. The partial amino acid sequence comprising a total of 45 amino acids from the N-terminal, is believed to be:

pyrGlu-Lys-Pro-Ala-Ala-Cys-Arg-Cys-Ser-Arg-Glx-
                5                          10

-Asx-Pro-Lys-Asx-Arg-Val-Asx-Cys-Gly-Phe-Pro-Gly-Ile-Thr-
      15                  20                      25

-Ser-Asx-Glx-Cys-Phe-Thr-Ser-Gly-Cys-Cys-Phe-Asx-Ser-Glx-Val-
          30                  35                      40

-Pro-Gly-Val-Pro-Trp-,
                                                         45 wherein pyrGlu (residue 1) stands for pyroglutamic acid.

In the meantime, it has been found that the whole amino acid sequence of PSP is believed to be:

pyr—Glu—Lys—Pro—Ala—Ala—Cys—Arg—Cys—Ser—
 1                      5

Arg—Gln—Asp—Pro—Lys—Asn—Arg—Val—Asn—Cys—
10                          15

Gly—Phe—Pro—Gly—Ile—Thr—Ser—Asp—Gln—Cys—
20                       25

Phe—Thr—Ser—Gly—Cys—Cys—Phe—Asp—Ser—Gln—
30                           35

Val—Pro—Gly—Val—Pro—Trp—Cys—Phe—Ser—Pro—
40                           45

Leu—Pro—Ala—Gln—Glu—Ser—Glu—Glu—Cys—Val—
50                           55

Met—Gln—Val—Lys—Ala—Arg—Lys—Asn—Ser—Gly—
60                           65

Tyr—Pro—Gly—Ile—Cys—Pro—Glu—Asp—Cys—Ala—
70                           75

Ala—Arg—Asn—Cys—Cys—Phe—Ser—Asp—Thr—Ile—
80                           85

Pro—Glu—Val—Pro—Trp—Cys—Phe—Phe—Pro—Met—
90                           95

Ser—Val—Glu—Asp—Cys—His—Tyr.
                    100                      105

The abbreviations for the amino acids are taken from J. Biol. Chem. 243 (1968), 3558.

The present invention also provides a method for preparing purified PSP, which method comprises isolating PSP from porcine pancreatic tissue after extraction to remove the insulin therefrom. PSP can be isolated from insulin salt cake by a combination of chromatography and precipitation processes. PSP also can be isolated from the mother liquor of the insulin salt cake. The preparation of an insulin salt cake is, *inter alia*, described in Ind.Eng.Chem. 32 (1940), 908, Diabetes Mellitus (Eli Lilly), 7 ed, 1967, 41, and Danish patent application No. 5851/72.

DISCUSSION OF THE INVENTION

The insulin salt cake may be prepared as follows:

Whole, neatly defatted porcine pancreas glands are finely comminuted under frozen conditions and then subjected to the conventional extraction process for recovery of insulin, that is extracted with a mixture of water and an organic water-miscible solvent, such as a lower aliphatic alkanol, for example ethanol or isopropanol, in an acid medium, for example a medium having a pH in the range of from about 1.5 to 5 when measured with a pH meter in the mixture. The acid pH is obtained by using an acid. In the mixture, the organic solvent is present in a concentration in the range of from about 40% to 80% (v/v) when all the components are mixed. The slurry is stirred at a temperature in the range of about 5° to ambient followed by removal of the gland residues, e.g., by centrifugation. The extract pH is adjusted to the range of from about 5 to 9. Then, after being clarified, for example by centrifugation, the extract is acidified to a pH in the range of from about 3 to 4, whereafter the extract is freed of any organic solvent, for example by evaporation at reduced pressure, followed by removal of lipid compounds, for example by centrifugation. Insulin admixed with other proteins and polypeptides including PSP, is salted out from the concentrated extract so obtained, usually by addition of sodium chloride to a concentration in the range of from about 10 to 30% (w/v); the precipitate which forms is isolated, for example by centrifugation, thus affording the insulin salt cake.

Recovery of PSP from Insulin Salt Cake

The salt cake thus obtained is dissolved in water and crude insulin isolated by isoelectric precipitation at a pH in the range of from about 4.9 to 5.7, for example about 5.3, optionally in the presence of metal ions, for example zinc ions. The insulin precipitate is recovered, usually by centrifugation. The supernatant is then given a higher pH in the range of from about 5.7 to 7, preferably about 6.5. The precipitate that forms, containing some insulin, is also centrifuged off. In order to remove ancillary substances, such as salts, an excess of EDTA is added to the insulin stripped supernatant, followed by the addition of a water-miscible organic solvent, preferably ethanol (usually from 5 to 20 volumes). The mixture is left overnight at about 4° C. and then centrifuged to recover precipitated material. The precipitate is dried *in vacuo*, yielding a dry powder, hereinafter referred to as "supernatant protein" that contains the PSP.

PSP can be obtained in a crude crystalline form from a solution of the "supernatant protein" in water (about 10 parts). The solution is stirred gently while acid, for example, acetic acid, is added in the course of about 3 hours until a pH in the range of from about 3.8 to 4.8, preferably about pH 4.3, is attained. The mixture is then chilled and the stirring is continued for 3 days, preferably at about 4° C. A crop of relatively large, bar-shaped, birefringent crystals is harvested, for example, by centrifugation, and then dried *in vacuo*.

The material so obtained may be further purified, preferably by applying consecutive steps of anion and cation exchange chromatography.

Referring now to the drawings.

Figure 2:
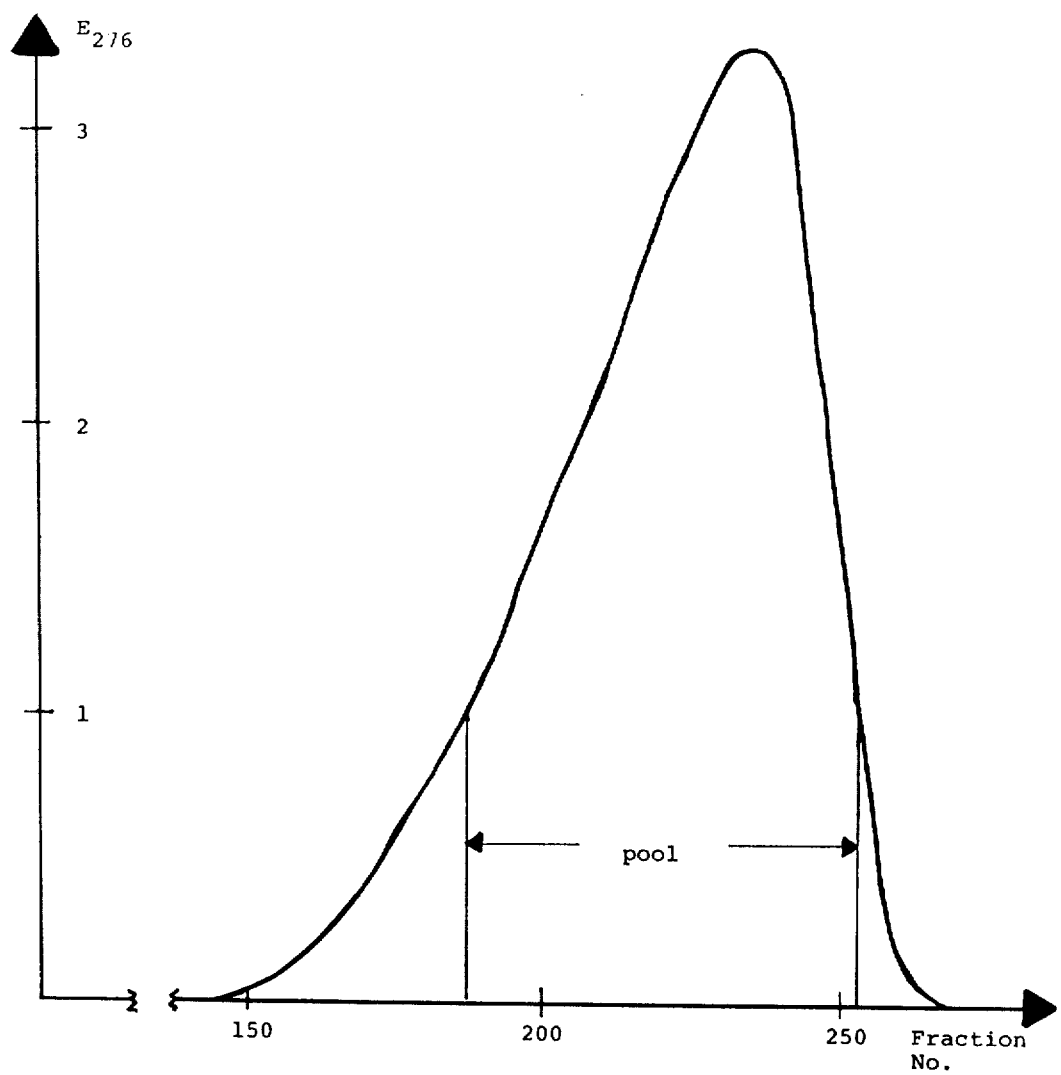

FIG. 1 illustrates the details of an exemplary anion exchange chromatographic purification of crude PSP; and, FIG. 2 illustrates the details of cation exchange chromatographic purification of the PSP fraction from the anion exchange purification of FIG. 1.

To illustrate the procedure, anion exchange chromatography may be performed on a column of "QAE-Sephadex A-25" (supplied by Pharmacia AB, Sweden), using the eluent stated on FIG. 1 of the accompanying drawings (TRIS being tris[hydroxymethyl]aminomethane).

The chromatogram obtained by monitoring the optical density of fractions at 276 nm shows one main peak. The pool corresponding to the main peak is adjusted to pH 7.4 and then mixed with a water-miscible organic solvent, for example ethanol (4 volumes). Upon standing at 4° C. for 2 days a precipitate is recovered by centrifugation and dried *in vacuo*.

The material so obtained can be further purified by cation exchange chromatography, for example on a column of "SP-Sephadex C-25" (supplied by Pharmacia). Elution may be effected with the eluent stated on FIG. 2 of the accompanying drawings. The chromatogram, obtained in the same manner as above, shows a main peak. Pooled fractions corresponding thereto are evaporated to dryness, the residue is dissolved in water at a pH in the range of from about 6 to 8, for example about 7, mixed with an excess (about 12 volumes) of a water miscible organic solvent, for example ethanol, and left overnight under similar conditions as described above. Purified PSP, which precipitates from the solution, is isolated by centrifugation, washed with ethanol, and dried *in vacuo*.

Recovery of PSP from Salt Cake Mother Liquor

Alternatively, or in addition, PSP containing protein may be obtained from the mother liquor arising when isolating the insulin salt cake by salting out with sodium chloride in a concentration of from 10 to 20% (w/v). The mother liquor is subjected to an additional salting out process, preferably with sodium chloride or ammonium sulphate.

The precipitate is recovered, for example by centrifugation. Purified PSP can be obtained from the precipitate by the use of anion and/or cation chromatography in any order.

Recovery of PSP from an unfractionated extract of pancreas

By a further method, PSP containing protein may be isolated from the above extract of pancreas glands obtained using a mixture of water and an organic water-miscible solvent by adsorption to a cation or anion exchanger, for example alginic acid, sulphonated polystyren or aminoethylcellulose. Thereafter, the ion exchanger is washed and the protein is eluted with an aqueous medium. The isolation by the use of an ion exchanger is performed by methods which are analogous to known methods.

PROPERTIES OF PSP

PSP obtained by any of the above methods has the following characteristics:

Molecular weight, calculated from the amino acid composition: about 11,700.

Molecular weight, determined by sodium dodecyl sulphate gel electrophoresis (Neville: J. Biological Chemistry 246 (1971) 6328): about 10,700.

Electrophoretic characteristics:

Basic DISC electrophoresis (basic DE) in polyacrylamide gel as described by J. Schlichtkrull et al. (Horm. Metabol. Research, Suppl. Series 5 (1974) 134) shows essentially a single band with $R_f$ 0.65–0.75. A similar pattern is obtained in analytical electrofocusing in polyacrylamide gel by which method the pI is determined to about 4.4.

Products obtained upon treatment of PSP with trypsin, α-chymotrypsin, CNBr, acid, or pyroglutamate aminopeptidase as described below, have a spasmolytic activity of the same order as that of PSP.

Trypsin treatment:

Twenty mg of PSP was dissolved in 20 ml of 0.01 M $NH_4HCO_3$ (pH: 7.8) and preincubated for 5 minutes at 37° C. After addition of 100 μl of 0.001 M HCl containing 0.4 mg TPCK-trypsin (obtained from Worthington Biochem.Corp.), the mixture was incubated at 37° C. for 15 minutes and then lyophilized.

α-Chymotrypsin treatment:

Twenty mg of PSP was dissolved in 200 μl of 0.1 M NaOH and 1800 μl of 0.05 M $NH_4HCO_3$ (pH: 8.0) was added. The solution was preincubated for 5 minutes at 37° C. and 50 μl of 0.001 M HCl containing 100 μg α-chymotrypsin (obtained from Sigma Chemical Company) was added. The incubation was continued for one hour at 37° C. and the reaction was stopped by the addition of 50 μl concentrated acetic acid, whereafter the solution was lyophilized.

CNBr treatment

Twenty mg of PSP was dissolved in 2 ml of 70% (v/v) formic acid containing 72 mg CNBr. The mixture was stored at room temperature for 40 hours and then lyophilized. The lyophilization was then repeated after addition of 2 ml of water.

Acid treatment

Samples of 1 mg PSP, dissolved in 100 μl of 0.5 N hydrochloric acid, were incubated at 37° C. for 2, 10 and 21 days. After incubation the protein of each sample was precipitated quantitatively by the addition of 2 ml of acetone. The precipitate was isolated by centrifugation, washed with 2 ml of acetone and dried in vacuo. The samples so obtained and a sample of untreated PSP were analysed by basic DE, vide supra, with the proviso that the time of electrophoresis was reduced to give $R_f$=0.53 for PSP. In the sample incubated for 2 days a series of bands were observed with $R_f$ ranging from 0.53 to 0.86. In the samples incubated for 10 and 21 days only a single band with $R_f$ 0.86 appeared. The results indicate that a partial deamidation of PSP had occurred after 2 days and a complete deamidation after 10 days of incubation.

Pyroglutamate aminopeptidase treatment

A sample of 6 mg of PSP was dissolved in 2 ml of 50 mM sodium monohydrogen phosphate, 30 mM p-mercaptoethanol, 1 mM EDTA buffer with a pH of 7.8. A solution of 2.5 mg of pyroglutamate aminopeptidase (obtained from Boehringer Mannheim) in 0.5 ml of the above buffer was added. The mixture was incubated for 16 hours at 37° C. and thereby lyophilized. (2.5 mg of pyroglutamate aminopeptidase used contained about 10 mU enzymatic activity.)

The purity of the final PSP product may be checked by analytical isoelectric focusing (IEF) and basic DISC electrophoresis (basic DE, vide supra). The product migrates essentially as a single band in both systems. IEF is performed according to the instructions of LKB brochure I-1804-E02: "LKB Ampholine PAG" plates for analytical electrofocusing on polyacrylamide gels (LKB-Produkter AB, Bromma, Sweden).

Likewise, gel filtration of the polypeptide on "Bio-Gel P-30" (supplied by Biorad Laboratories, Richmond, Calif., U.S.A.) using 1 molar acetic acid as the eluent, reveals only a single peak.

PSP has been analyzed for a number of immunoreactivities according to methods known in the art. The results obtained are presented in Table 1:

TABLE 1

| Immunoreactant | Contents (ppm) |
|---|---|
| Insulin (IRI) | 3–6 |
| Total glucagon (total GLI) | <0.02 |
| Pancreatic glucagon (pancreatic GLI) | <0.02 |
| Vasoactive intestinal peptide (VIP) | <0.02 |
| Pancreatic polypeptide (porcine) | ~0.08 |
| C—Peptide (porcine) | <0.1 |
| Somatostatin | ~0.002 |

The immunoreactivity of PSP is measured by a highly specific radioimmunoassay which is developed to detect down to 250 pg per ml.

Antibodies were prepared by immunizing rabbits with "supernatant protein" (0.5 ml of a solution containing approximately 4 mg protein per ml) mixed with Freund's adjuvant (0.5 ml) twice weekly for a period of 26 weeks. Beginning from the 13th day after the first immunization, a total of 10 blood samples (10 ml) from each animal, taken at regular intervals over a period of 172 days, were collected. The antisera obtained were tested for affinity and capacity and a suitable antiserum was selected for use in the radioimmunoassay. $^{125}$I-PSP was prepared by the lactoperoxidase method developed by Thorell and Johansson (Biochim.Biophys.Acta 251 (1971) 363). The radioiodinated PSP was purified by anion exchange chromatography as known in the art and used for polypeptide radioimmunoassay according to the procedure developed by L. G. Heding (Diabetologica 7 (1971), 10).

Furthermore, the present invention relates also to physiologically acceptable salts of PSP and, as examples of such salts, salts with cations such as sodium, potassium, magnesium, calcium and zinc and acid addition salts with organic or inorganic acids such as formic, methansulfonic, hydrochloric and sulphuric acid, can be mentioned. For the sake of brevity, the designation PSP Compounds is used to cover PSP and physiologically acceptable salts thereof.

UTILITY OF PSP

PSP and glucagon were found to be about equipotent in their inhibition of the amplitude of the contractions of electrically stimulated guinea pig ileum in vitro, vide Table 2. PSP and glucagon were dissolved in 0.9% sodium chloride with 0.1% human serum albumin.

TABLE 2

| Concentration in the organ bath, M | Inhibitory effect in per cent | |
|---|---|---|
| | PSP | Glucagon |
| $10^{-5}$ | 89 | 89 |
| $10^{-6}$ | 49 | 51 |
| $10^{-7}$ | 21 | 24 |

This effect of PSP was blocked by phentolamine but not by naloxone. The spontaneous motility of the isolated ileum from reserpine-treated guinea pigs was inhibited by PSP.

Likewise, PSP Compounds were found to be about as potent as glucagon with respect to its inhibition in vivo of the peristalsis in mice, *vide* Table 3, an effect which again could be blocked by phentolamine.

TABLE 3

| Drug (50 mg/kg subcutaneously) | Percent of intestine traversed by charcoal compared to a control |
| --- | --- |
| PSP | 78 |
| Glucagon | 66 |
| Atropinsulphate | 64 |

PSP reduces intestinal motility in rabbits *in vivo* after administration intravenously or intraluminally in the intestine. The motility was recorded by means of a balloon catheter in the intestine connected to a pressure transducer. In 5 out of 5 rabbits (from 2.5 to 3.0 kg body weight) 400 µg PSP administered intravenously or 5 cm from the balloon into the lumen of the intestine caused a marked reduction of the intestinal motility, almost to atonia. 200 µg had a clear effect in 3 out of 5 rabbits. Glucagon had the same effect, but only when administered intravenously.

PSP was found to delay the absorption of [U−$^{14}$C] protein hydrolysate in pigs and in pancreatectomised dogs and of [U−$^{14}$C] ovalbumin in pancreatectomised dogs, when the compound was administered perorally in a capsule with 3 mg PSP. The pigs and the dogs weighed about 30 kg. 100 µCi [U−$^{14}$C] protein hydrolysate or 5 µCi [U−$^{14}$C] ovalbumin was mixed with a suspension of 1 g/kg Idon ® and administered through stomach tubes. Maximum plasma dpm values were reached from 30 to 40 minutes later after administration of PSP as compared to placebo. This delay in absorption caused by about 100 µg/kg of PSP orally probably reflects a reduced gastro-intestinal motility.

PSP was found to inhibit pentagastrin stimulated gastric acid secretion in rats and cats with chronic gastric fistulas. 10 µg PSP infused over 1 hour to rats was found to be as effective in inhibiting the acid secretion after 5 µg pentagastrin s.c. as 1 µg somatostatin, i.e. the peptides are almost equipotent on a molar basis. 10 µg/kg PSP s.c. and 250 µg PSP orally in a capsule were effective in cats.

PSP Compounds were found to be devoid of any *in vitro* effect on the release of glucagon or insulin or on lipolysis and of any *in vivo* effect on blood glucose. Nor did an intravenously injected dose of up to 1 mg/kg exert any significant effect on the blood pressure of the anesthetized rat.

The above pharmacological data indicate the value of PSP Compounds for the treatment and prevention of smooth muscle spastic conditions, for example in the intestine. Due to the lack of metabolic effects, PSP Compounds may prove advantageous as a substitute for glucagon in endoscopy and in radiological procedures.

Besides the data indicate the value of PSP in the treatment of increased gastrointestinal motility and gastroduodenal ulcers.

PSP compounds may be administered intravenously as a bolus or as an infusion. When an effect of prolonged nature, slower in onset, is desired, PSP Compounds may be administered as a depot from which it is slowly mobilized by the blood stream such as intramuscularly or subcutaneously in a region of good peripheral circulation supply. The fact that the biological activity and the immunoreactivity is maintained after exposure of PSP to gastric juice, trypsin, and chymotrypsin and the experiments described above showing delayed absorption and inhibition of gastric acid secretion after oral administration of PSP points to the oral route as a possible way of administration. Therefore, PSP may be administered through an endoscope during the endoscopy procedures or PSP may be mixed with the contrast media, e.g. barium sulphate, during the radiology procedure. PSP may be administered orally in capsules to patients with gastroduodenal ulcers.

The dosage rates of PSP Compounds can be adjusted according to the magnitude of desired response and other factors routinely taken into consideration in establishing the dosage. As an example of a dosage range, from 10 to 200 µg per kg body weight can be mentioned, although a lower or higher dosage may be administered.

The present invention also relates to a pharmaceutical composition comprising PSP Compounds and one or more pharmaceutically acceptable carrier(s). As examples of such carriers, an aqueous solution of 0.9% sodium chloride can be mentioned. Optionally, preservatives such as methyl or ethyl parabene or phenol may be included in the composition. Said composition may contain 0.1–200 mg per ml, preferably 0.5–25 mg per ml of PSP.

To be more certain that the desired result is obtained after administration of a PSP Compound it is advisable to use as starting material for preparing PSP containing pharmaceutical compositions a PSP compound which has a purity of at least 50%, preferably a purity of at least 90% by dry weight. Preferred is highly purified PSP. Highly purified PSP is PSP which essentially migrates as a single band in the above IEF and basic DE systems.

According to hitherto unpublished data pancreatin pills contain PSP (for example, about 1 part per thousand). Because of its content of enzymes, pancreatin pills have been used for pancreatectomized patients and patients with chronic pancreatitis. Commercial insulin has now been found to contain about 30 ppm PSP.

DETAILED PRACTICE OF THE INVENTION

The following Examples, which, however, are not considered to be limiting on the practice of this invention, are presented to illustrate the process for preparing PSP.

EXAMPLE 1

A salt cake originating from 94 kg of porcine pancreas glands was dissolved in water to a volume of 3.2 liters. The pH of the solution was adjusted to 5.3, whereafter the insulin containing precipitate was removed by centrifugation. The pH of the supernatant was adjusted to 6.5 and the suspension thus formed was centrifuged. The solution was mixed with 32 ml of 0.5 M Na$_4$EDTA and 35 liters of ethanol. The mixture was left overnight at 4° C. and then centrifuged. The precipitate was dried *in vacuo* yielding 50 g of dry supernatant protein powder.

A solution of the supernatant protein powder in 500 ml of water was stirred gently while 1 M acetic acid was added slowly by means of a peristaltic pump until a pH of 4.30 was attained (after about 3 hours of pumping). Stirring was then continued for 3 days at 4° C. whereby crystallization occurred. The crop of crystals (bar-shaped by appearance, possibly orthorhombic and showing birefringence) were harvested by centrifugation, suspended in 500 ml of water at 4° C. with stirring overnight, centrifuged and dried *in vacuo.* The yield was 5.2 g.

4 g of this material was dissolved in 50 ml of 50 percent (v/v) ethanol and 50 ml of eluent (*vide* FIG. 1) at pH 8.6. The solution was subjected to anion exchange chromatography as shown in FIG. 1. The pool from the main peak was given a pH of 7.4, mixed with 4 volumes of 96 percent (v/v) ethanol and then stored at 4° C. for 2 days. The precipitate was isolated by centrifugation, washed twice with 150 ml of 96 percent (v/v) ethanol and dried *in vacuo.* The yield was 2.6 g.

2.5 g of this material was dissolved in 125 ml of 50 percent (v/v) ethanol and 125 ml eluent (*vide* FIG. 2) at pH 4.7 and then subjected to a cation exchange chromatography as shown in FIG. 2. The pool from the main (only visible) peak was evaporated to dryness. The residue was dissolved in water and the pH of the solution was adjusted to 7.1 (the final volume was about 90 ml). The solution was mixed with 1200 ml of 96 percent (v/v) ethanol and the mixture was stored at 4° C. overnight. The precipitate was isolated by centrifugation, washed twice with 150 ml of 96 percent (v/v) ethanol, and dried *in vacuo.* The yield was 1.8 g of highly purified PSP fulfilling the purity requirements stated in Table 1.

EXAMPLE 2

20 g of supernatant protein powder, produced as described in Example 1, was dissolved in 200 ml of water. 208 ml of 96 percent (v/v) ethanol was added, followed by adjustment of pH to 4.6 with acetic acid. A small precipitate was removed by centrifugation. The supernatant, which slowly became turbid, was subjected to cation exchange chromatography on a 2.5×80 cm column of "SP-Sephadex C-25," equilibrated in Eluent 1 (0.4 M acetic acid, 0.05 M sodium acetate, 50 percent (v/v) ethanol, pH: 4.6). Linear gradient elution was performed between 3 l of Eluent 1 and 3 l of Eluent 2 (0.3 M sodium acetate, 50 percent (v/v) ethanol, pH: 8.7). Fractions of 10 ml were collected at an elution rate of 40 ml/h. The fractions corresponding to the large peak appearing from fractions 100 to 130 were pooled. The pool was given a pH of 8 and then mixed with 1.8 l of 96 percent (v/v) ethanol. The mixture was stored at 4° C. for 24 hours. The precipitated protein was isolated by centrifugation, washed twice with 150 ml of 96 percent (v/v) ethanol and dried *in vacuo.* Yield: 2.8 g. 2.5 g of this material was dissolved in 250 ml of a TRIS buffer (0.0575 M TRIS, 0.05 N HCl, pH: 7.4.). The solution was subjected to anion exchange chromatography on a 2.5×50 cm column of "QAE-Sephadex A-25," equilibrated in a TRIS buffer (0.115 M TRIS, 0.1 N HCl, pH: 7.4). The column was eluted with the equilibration buffer at a rate of 30 ml/h. Fractions of 10 ml were collected. The fractions corresponding to the central major part of the peak showing a maximum at fraction 225 were pooled. The pool (620 ml) was mixed with 60 ml of 5 M sodium chloride and 12 l of 96 percent (v/v) ethanol. The mixture was stored at 4° C. for 24 hours. The precipitated protein was isolated by centrifugation, washed twice with 150 ml of 96 percent (v/v) ethanol and dried *in vacuo.* Yield: 1.7 g of highly purified PSP.

EXAMPLE 3

To 150 liters of an aqueous solution obtained by evaporation of an extract from 250 kg of porcine pancreas glands and which was feed from insoluble material, 22.5 kg of sodium chloride were added. The mixture was stirred to dissolve the salt added and the resulting precipitate was removed by centrifugation, thus affording the insulin salt cake. To the mother liquor (162 liters) was added 34 kg of ammonium sulphate; continued stirring for 2 hours at room temperature afforded a precipitate which was isolated by centrifugation. 223 g of the wet product were dissolved by addition of 500 ml of a buffer (0.05 M formic acid, 0.01 M sodium hydroxide buffer, pH: 3.2). The conductivity of the solution was reduced to 4 mS by dialysis against water. The solution was applied on a 5×50 cm column of "SP-Sephadex C-25" equilibrated with Buffer I (0.1 M formic acid, 0.02 M sodium hydroxide, pH: 3.2). After application of the solution, the column was eluted with a linear gradient of sodium chloride from 0 to 0.27 M in Buffer I. The total volume of the eluent was 5.5 l. The column was then further eluted with Buffer I containing 0.27 M sodium chloride. The flow during the application and elution was 100 ml per hour and fractions of 15 ml were collected. The chromatogram obtained by monitoring the optical density of the fractions at 276 nm showed one main peak from fraction 420 to 530. The pool corresponding to the main peak was adjusted to a pH of 7.4 and then mixed with 20 volumes of 96 percent (v/v) ethanol. Upon standing at 4° C. for 48 hours, a precipitate was recovered by centrifugation and dried *in vacuo.* Yield: 6 g. The material so obtained was further purified by anion exchange chromatography on a column of "QAE-Sephadex A-25," as described in Example 2. Yield: 3.4 g of highly purified PSP.

EXAMPLE 4

A preparation for parenteral administration containing 1 mg of PSP per ml may be prepared as follows:

1 g of PSP and 99 g of lactose are dissolved in 1 liter of destilled water and the pH is adjusted to 7.0. The solution is thereafter steril filtered. The sterile solution is filled in 10 cc vials in such a way that each vial contains 10 ml of the solution. Thereafter, the solutions are lyophilised and the vials are sealed at aseptic conditions.

The preparation in any of the vials is to be dissolved in 10 ml of sterile water before administration.

EXAMPLE 5

Oral preparations may be prepared as follows:

100 mg of PSP is admixed with 9 g of maize starch, 8 g of lactose, and 180 mg magnesium stearate until a homogeneous mixture is obtained. The mixture is filled in hard gelatine capsules No. 3 in such a way that each capsule contains 1 mg of PSP.

We claim:

1. A polypeptide exhibiting the following amino acid composition:

pyrGlu-Lys-Pro-Ala-Ala-Cys-Arg-Cys-Ser-Arg-
1                         5                        10

-Gln-Asp-Pro-Lys-Asn-Arg-Val-Asn-Cys-Gly-
15                       20

-Phe-Pro-Gly-Ile-Thr-Ser-Asp-Gln-Cys-Phe-
25                       30

-Thr-Ser-Gly-Cys-Cys-Phe-Asp-Ser-Gln-Val-
35                       40

-Pro-Gly-Val-Pro-Trp-Cys-Phe-Ser-Pro-Leu-
45                       50

-continued

-Pro-Ala-Gln-Glu-Ser-Glu-Glu-Cys-Val-Met-
55                                     60

-Gln-Val-Lys-Ala-Arg-Lys-Asn-Ser-Gly-Tyr-
65                                     70

-Pro-Gly-Ile-Cys-Pro-Glu-Asp-Cys-Ala-Ala-
75                                     80

-Arg-Asn-Cys-Cys-Phe-Ser-Asp-Thr-Ile-Pro-
85                                     90

-Glu-Val-Pro-Trp-Cys-Phe-Phe-Pro-Met-Ser-
95                                    100

-Val-Glu-Asp-Cys-His-Tyr
105 wherein pyrGlu (residue 1) stands for pyroglutamic acid, and the physiologically acceptable salts thereof.

2. The polypeptide according to claim 1 in crystalline form.

3. A human purposes medicament or diagnostic composition which comprises an effective amount of the polypeptide of claim 1 or the physiologically acceptable salts of the said polypeptide therein in associaton with a physiologically acceptable carrier.

4. The composition of claim 3 further comprising for carrier an aqueous sterile solution containing about 0.9% sodium chloride and optionally a preservative, the said polypeptide being present in a concentration of from 0.1 to 200 mg per ml.

5. A method of treatment to relax the human gastrointestinal tract which comprises administering the composition of claim 3 in an effective dosage.

6. The method of treatment of claim 5 further comprising administering the composition orally.

7. A method of treatment to relax the human gastrointestinal tract and to reduce the secretion of gastric acid which comprises administering the polypeptide of claim 1 in an effective dosage.

8. The method of treatment of claim 7, further comlprising administering the composition orally.

9. A method for isolating a polypeptide of the following amino acid composition:

pyrGlu-Lys-Pro-Ala-Ala-Cys-Arg-Cys-Ser-Arg-
1              5                      10

-Gln-Asp-Pro-Lys-Asn-Arg-Val-Asn-Cys-Gly-
15                                    20

-continued

-Phe-Pro-Gly-Ile-Thr-Ser-Asp-Gln-Cys-Phe-
25                                     30

-Thr-Ser-Gly-Cys-Cys-Phe-Asp-Ser-Gln-Val-
35                                     40

-Pro-Gly-Val-Pro-Trp-Cys-Phe-Ser-Pro-Leu-
45                                     50

-Pro-Ala-Gln-Glu-Ser-Glu-Glu-Cys-Val-Met-
55                                     60

-Gln-Val-Lys-Ala-Arg-Lys-Asn-Ser-Gly-Tyr-
65                                     70

-Pro-Gly-Ile-Cys-Pro-Glu-Asp-Cys-Ala-Ala-
75                                     80

-Arg-Asn-Cys-Cys-Phe-Ser-Asp-Thr-Ile-Pro-
85                                     90

-Glu-Val-Pro-Trp-Cys-Phe-Phe-Pro-Met-Ser-
95                                    100

-Val-Glu-Asp-Cys-His-Tyr
105 wherein pyrGlu (residue 1) stands for pyroglutamic acid, which comprises extracting porcine pancreas glands with a mixture of water and a water miscible solvent under extraction conditions adapted to recover insulin from the glands, then evaporating the water miscible solvent from the extract, followed by removal of lipid compounds therefrom, and thereafter recovering the above-described polypeptide from the extract so obtained, by separating the extract into a portion thereof more enriched in said polypeptide followed by chromatographic purification and concentration of the said polypeptide enriched fraction until a fraction results wherein said polypeptide comprises at least 50 percent by dry weight.

10. A method according to claim 9, characterized in that insulin and accompanying proteins are salted out after the removal of said lipid compounds, that the salt cake is dissolved in water, that the resulting solution is given a pH between 4.9 and 5.7, and that the precipitate formed is removed, whereafter said polypeptide is recovered from the so treated solution.

11. A method according to claim 9, characterized in that insulin and accompanying proteins are salted out after the removal of lipid compounds, and that the salt cake formed is removed, whereafter said polypeptide is recovered from the so treated extract.

* * * * *